United States Patent
Soomro et al.

(10) Patent No.: US 9,762,648 B2
(45) Date of Patent: Sep. 12, 2017

(54) PATIENT MONITORING OVER HETEROGENEOUS NETWORKS

(75) Inventors: Amjad A. Soomro, Hopewell Junction, NY (US); Ruediger Schmitt, Maplewood, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 967 days.

(21) Appl. No.: 13/636,242

(22) PCT Filed: Mar. 15, 2011

(86) PCT No.: PCT/IB2011/051082
§ 371 (c)(1),
(2), (4) Date: Sep. 20, 2012

(87) PCT Pub. No.: WO2011/124996
PCT Pub. Date: Oct. 13, 2011

(65) Prior Publication Data
US 2013/0021169 A1   Jan. 24, 2013

Related U.S. Application Data

(60) Provisional application No. 61/321,902, filed on Apr. 8, 2010.

(51) Int. Cl.
*G08C 15/06* (2006.01)
*H04L 29/08* (2006.01)
(Continued)

(52) U.S. Cl.
CPC ......... *H04L 67/06* (2013.01); *G06F 19/3418* (2013.01); *H04L 67/12* (2013.01);
(Continued)

(58) Field of Classification Search
CPC ...................................................... G01D 4/004
(Continued)

(56) References Cited

U.S. PATENT DOCUMENTS

| | | |
|---|---|---|
| 6,614,808 B1 | 9/2003 | Gopalakrishna |
| 2002/0009053 A1* | 1/2002 | Sjoblom .................. 370/235 |

(Continued)

FOREIGN PATENT DOCUMENTS

| | | |
|---|---|---|
| EP | 1892917 B1 | 2/2009 |
| JP | 2010011188 A | 1/2010 |
| WO | 2004109992 A1 | 12/2004 |

OTHER PUBLICATIONS

Rosenberg, et al "Standards Track" RFC3261—SIP: Session Initiation Protocol Copyright 2002 the Internet Society pp. 1-269.
Berggren, M.; Wireless communication in telemedicine using Bluetooth and IEEE 802.11b; 2001; Uppsala Master's Thesis; http://user.it.uu.se/perg/wifi-bluetooth-interference.pdf.
(Continued)

*Primary Examiner* — Toan N Pham
*Assistant Examiner* — Israel Daramola (57) ABSTRACT

A patient monitor includes least one monitoring device which collects patient data about a patient. A packet generator generates data packets from the patient data collected from the patient. A communication unit transmits the data packets over an Internet protocol (IP) network. The communication unit includes a first transmitter for transmitting the data packets using a first wireless network and a second transmitter for transmitting the data packets using a second wireless network.

20 Claims, 11 Drawing Sheets

(51) Int. Cl.
  *G06F 19/00* (2011.01)
  *H04L 29/06* (2006.01)
(52) U.S. Cl.
  CPC .......... *H04L 67/2823* (2013.01); *H04L 69/14* (2013.01); *H04L 69/16* (2013.01); *H04L 69/161* (2013.01); *H04L 69/18* (2013.01); *H04L 69/166* (2013.01); *H04L 69/22* (2013.01); *Y02B 60/33* (2013.01)
(58) Field of Classification Search
  USPC ...................... 370/230.1, 235, 241, 252, 338
  See application file for complete search history.

(56) References Cited

U.S. PATENT DOCUMENTS

| | | | |
|---|---|---|---|
| 2003/0100308 A1 | 5/2003 | Rusch | |
| 2004/0010616 A1 | 1/2004 | McCanne | |
| 2004/0170154 A1* | 9/2004 | Carter et al. | 370/338 |
| 2008/0219281 A1 | 9/2008 | Akin et al. | |
| 2009/0086759 A1 | 4/2009 | Heise et al. | |
| 2009/0245114 A1* | 10/2009 | Vijayaraghavan | 370/241 |
| 2009/0274149 A1 | 11/2009 | Williams et al. | |
| 2010/0271944 A1* | 10/2010 | Michaelis et al. | 370/230.1 |
| 2011/0026406 A1* | 2/2011 | Gamage | H04L 43/106 370/241 |
| 2013/0163446 A1* | 6/2013 | Kruger et al. | 370/252 |

OTHER PUBLICATIONS

Schulzrinne, et al. "Application-Layer Mobility Using SIP" Mobile Computing and Communications Review, V. 4, No. 3, pp. 47-57.
Boysen, et al. "Proactive Handover Using SIP", Unclassified/Unlimited RTO-MP-INS-083 pp. 17-1-17-10.
Banerjee, et al. "Seamless SIP-Based Mobility for Multimedia Applications", IEEE Network Mar./Apr. 2006, pp. 6-13.
Yuce, et al., "A Wireless Medical Monitoring Over a Heterogeneous Sensor Network", Proceedings of 29th Annual Int'l Conference of IEEE EMBS, Lyon France, Aug. 23-26, 2007 pp. 5894-5898.
Belghoul, et al., "IP-Based Handover Management Over Heterogeneous Wireless Networks", Proceedings of 28th Annual EIII Int'l Conference on Local Computer Networks (LCN'03) 2pp.
Kawaguchi, et al., "NAT Free Open Source 3D Video Conferencing Using SAMTK and Application Layer Router", 978-1-4244-2309-5/09/$25.00 (c) 2009 IEEE, 2pp.
Niyato, et al., "Remote Patient Monitoring Service Using Heterogeneous Wireless Access Networks: Architecture and Optimization", IEEE Journal on Selected Areas in Communications, vol. 27, N. 4, May 2009, pp. 412-423.
Mies, et al., "Towards End-To-End Connectivity for Overlays Across Heterogeneous Networks", 978-1-4244-3437-4/09/$25.00 (c) 2009 IEEE, 6pp.
Wedlund E., et al.; Mobility Support Using SIP; 1999; WOWMOM; ACM Int'l Workshop on Wireless Mobile Multimedia; NY; pp. 76-82.

* cited by examiner

PATIENT MONITORING OVER HETEROGENEOUS NETWORKS

CROSS REFERENCE TO RELATED APPLICATIONS

This application claims the benefit of U.S. provisional application Ser. No. 61/321,902 filed Apr. 8, 2010, which is incorporated herein by reference.

The following relates to the medical arts, communication arts and related arts. It finds particular application in improving the communication in medical monitoring systems, medical alarm systems, and the like, through underlying networks in hospitals, urgent care centers, homes, nursing homes, assisted care facilities, emergency medical transportation vehicles and systems, and the like.

Presently, patient monitoring systems include one or more patient monitoring devices (PMD), a patient information display and storage system, and auxiliary patient information display systems. Physiological data collected from a patient by the PMD is transmitted to a patient information display system where the patient's physiological data is displayed or to a patient data storage system that stores the patient's physiological data. The patient's physiological data can also be viewed on auxiliary patient information display systems. For example, a nurse may view a patient's physiological data on another patient's bedside monitor, a central monitoring station, a PDA, or the like. The data transmission from the PMD to the patient information display and storage systems or from the patient information display and storage systems to auxiliary patient information display system traverses local area networks such as an Ethernet, IEEE802.11, and other Internet Protocol (IP) centric access networks (General Packet Radio Service (GPRS), CDMA 2000, Wireless LAN, mobile WIMAX).

A problem exists where more than one network may be available to provide communication between the PMD, the patient information display and storage systems, and the auxiliary patient information display systems. It is desirable to use any of the available networks to transmit data. For example, use of multiple networks is advantageous when various PMDs and systems are mobile and different networks provide coverage in different areas. However, connecting to a different network typically results in assigning a new IP address to the PMDs or the patient information display and storage systems or the auxiliary patient information display systems. A new IP address could also be assigned if a network connection is re-established due to earlier dropout of the connection on the same network.

Reassignment of a different IP address to a PMD or an auxiliary patient information display system could result in a discontinuity of data being transmitted to/from patient data display and storage systems due to breaks in underlying communication sessions. More importantly, the discontinuity could result in not detecting patient's adverse health condition for timely action by clinicians. Another problem occurs when mobile PMDs or auxiliary information display systems are moved behind firewalls. Typically, firewalls have Network Address Translators (NATs) which can alter the IP addresses and port numbers assigned to the PMDs or auxiliary information display systems. The resulting ambiguity in IP addresses or port numbers often results in session establishment failures with the other communicating party. A failure in connection establishment leads to discontinuity of data being transmitted to/from the patient data display and storage systems.

Another problem exists when the different networks have different bandwidths, delays, maximum supported packet sizes, bit error rates, or power consumption characteristics. Typically, for networks with higher bandwidths or data rates, it is advantageous to transmit packets with large number of bytes, but less frequently, to conserve power consumption. For a network which has higher bit error rates, it is more advantageous to transmit smaller packets and less inter-packet arrival rates. Conversely, networks which have low bit error rate, it is more advantageous to transmit bigger packets with large packet inter-arrival rate. Therefore, for a given network, there is an optimal packet size and inter packet generation delay for a given network characteristics.

For medical data, it is important not to lose data during a handoff from one wireless access point to another. This can be particularly problematic when the access points function with different communication characteristics.

The present application provides new and improved patient monitoring systems and methods which overcomes the above-referenced problems and others.

In accordance with one aspect, a method for transmitting physiological data is provided. A communication link is established between a multi-mode patient monitoring device and a plurality of Internet protocol (IP) networks. Physiological data is collected by the patient monitoring device. Data packets are generated from the collected physiological data. The generated data packets are duplicated. The duplicated data packets are transmitted over the plurality of networks. The transmitted duplicated data packets are received and a single set of data from the duplicated data packets is forwarded to an end application.

In accordance with another aspect, a patient monitor is provided. At least one monitoring device collects patient data about a patient. A packet generator generates data packets from the patient data collected from the patient. A communication unit transmits the data packets over an Internet protocol (IP) network, wherein the communication unit includes a first transmitter for transmitting the data packets using a first wireless network and a second transmitter for transmitting the data packets using a second wireless network.

One advantage resides in the consistent delivery of physiological data using existing wireless and wired infrastructures.

Another advantage resides in optimized power consumption, network utilization, and quality of service in the delivery of physiological data using existing wireless infrastructure.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
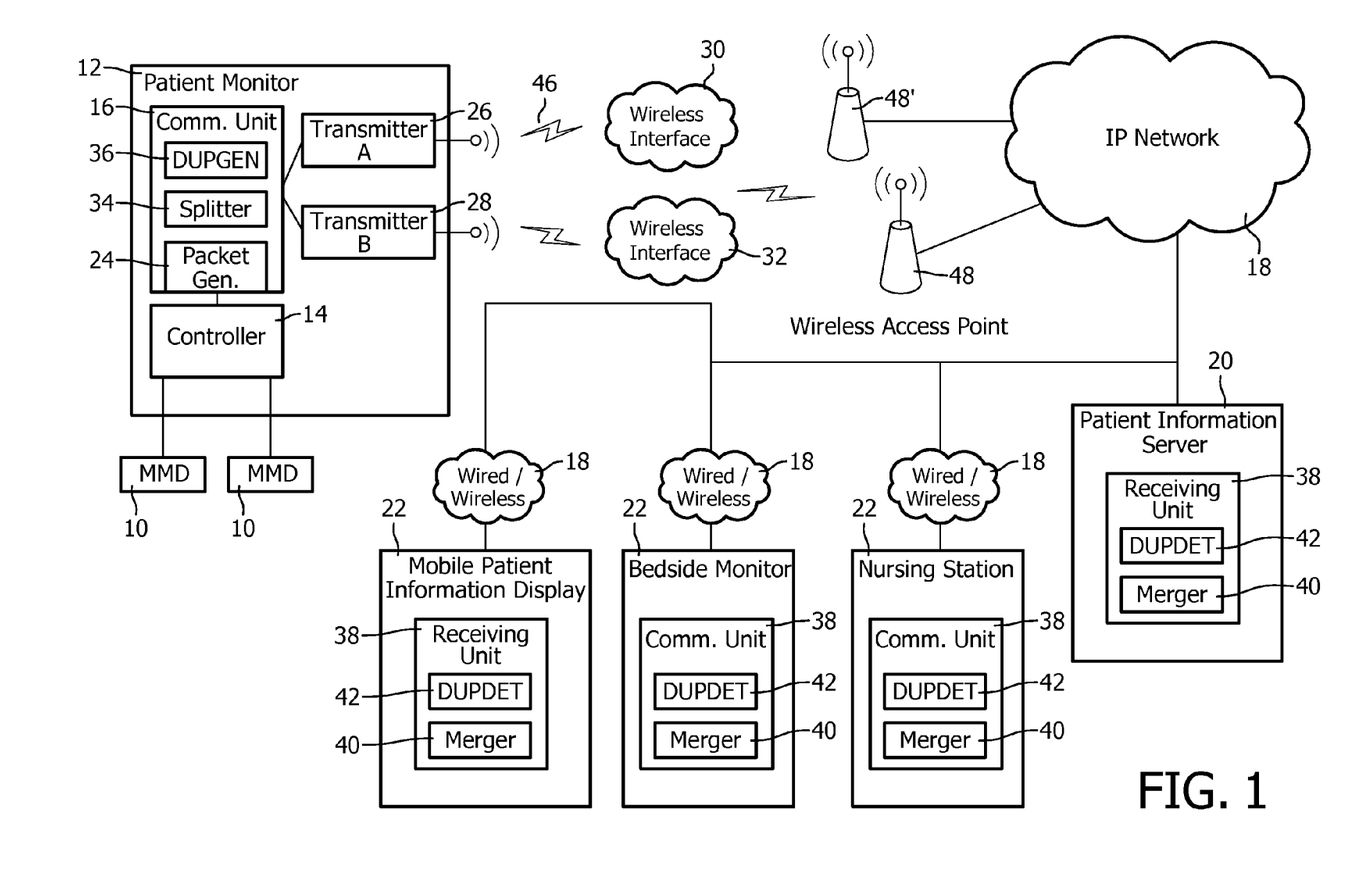
FIGS. 1 and 2 are diagrammatic illustrations of a patient monitoring system in accordance with the present application.

With reference to FIG. 1, a patient (not shown) is monitored by various medical monitoring devices or sensors 10 that measure physiological parameters of the patient and generate physiological data indicative thereof. These medical monitoring devices 10 may include an electrocardiographic (ECG) instrument with ECG electrodes, and a wrist-based medical monitor, which may for example be configured to monitor blood pressure, blood oxygenation (Sp02), pulse, or one or more other physiological parameters. Other medical monitoring devices 10 can be associated with a patient, and not all of the above-mentioned medical monitoring devices 10 have to be associated with a patient at any given time. It should be appreciated that while only two medical monitoring devices 10 are illustrated, more medical monitoring devices are contemplated. As used herein, medical monitoring devices signify data sources indicating patient health, such as devices that monitor pulse, blood oxygen, ECG, and other vital signs, or the like. Electronics for receiving signals from the medical monitoring device 10 and for optionally performing signal processing on such signals are embodied in the illustrated embodiment as a multi-functional patient monitor device (PMD) 12, or may be embodied partly or wholly as on-board electronics disposed with one or more the medical monitoring devices 10 or so forth. It should also be appreciated that the medical monitoring devices 10 and the PMD 12 could also be embodied into a single device. The PMD 12, for example, may be a monitor that travels with the patient, such as the transmitter of an ambulatory patient worn monitoring system, or the like.

The medical monitoring devices 10 report the measured or other physiological data to the PMD 12. The PMD 12 serves as a gathering point for the physiological data measured by the medical monitoring devices 10, and provides temporary storage for the data. The collected physiological data is concurrently transmitted to a controller 14 in the PMD 12. The PMD 12 also includes a communication unit 16 for transmitting the physiological data wirelessly through a hospital network 18 to a patient information server 20 where the patient's physiological data is displayed and stored. The patient's physiological data can also be transmitted through the hospital network 18 to mobile patient information display systems 22. For example, a nurse may view the patient's physiological data on the patient's bedside monitor, another patient's bedside monitor, a central monitoring station, a PDA, or the like. It should be appreciated that while only three mobile patient information displays 22 are illustrated, more mobile patient information displays are contemplated.

The communication unit 16 includes a packet generator 24 which generates data packets from the patient's physiological data that are transmitted over the hospital network 18. The communication unit controls a first transmitter 26 and a second transmitter 28 to transmit the physiological data, received by the controller 14, in the form of data packets on multiple wireless networks or wireless communication interfaces through the hospital network 18 to the patient information server 20 and the mobile patient information displays 22. The first transmitter 26 transmits the data packets to the hospital network 18 through a first wireless communication interface 30 and the second transmitter 28 transmits data packets through a second wireless communication interface 32. The wireless communication interfaces may include different IP centric access networks such as IP Multimedia Subsystem (IMS) GPRS, UMTS, CDMA2000, IS-95, GSM, CDMA, CDMA 1×, CDMA 1×EV-DO, WiMAX, IEEE 802.11, IEEE 802.15, IEEE 802.16, IEEE 802.21, Wi-Fi, UMTS over W-CDMA, UMTS over TDD, CDMA 3×EV-DO, HSPA D, HSPA U, EDGE, Bluetooth, Zigbee, UWB, LTE, Wi-Bree, or the like. It should be appreciated that while only two transmitters 26, 28 and two wireless communication interfaces 30, 32 are illustrated; more transmitters and wireless communication interfaces are contemplated.

The communication unit 16 also includes a packet splitting unit (splitter) 34 and packet duplicating unit (DUPGEN) 36. In one embodiment, the DUPGEN 36 creates duplicates of the data packets created by the packet generator 24 and the communication unit 16 controls the first transmitter 26 and the second transmitter 28 to transmit duplicate data packets on multiple wireless communication interfaces through the hospital network 18 to the patient information server 20 and the mobile patient information displays 22. In another embodiment, the splitter 34 modifies the duplicate data packets created by the DUPGEN 36 by resizing the data packet to the most appropriate packet size for each communication interface. The determination of the most appropriate packet size, and inter-arrival delay, for each communication interface depends on the each interface's power consumption characteristics, bandwidth and bit error rate, the application delay requirements, and the interface's maximum transmission units (MTU) size among others. The modified duplicate data packets are then transmitted through the hospital network 18 to the patient information server 20 and the mobile patient information displays 22 by the first transmitter 26 and the second transmitter 28 using multiple wireless communication interfaces.

From the hospital network 18, the data packets are transmitted through wired or wireless communication interfaces to the patient information server 20 and the mobile patient information displays 22. The patient information server 20 and the mobile patient information displays 22 each include a receiving unit 38 for receiving the transmitted data packets from the hospital network 18. The receiving units 38 include a packet merging unit (merger) 40 and a duplicate detection unit (DUPDET) 42. In one embodiment, the merger 40 merges together the modified data packets generated by the splitter 34 into a single data stream that accurately represents the data packets that entered the splitter 34. The DUPDET 42 then receives the duplicate data packets that were transmitted over the multiple wireless communication interfaces 30, 32 and forwards only one copy of the data packet to the endpoint application, for example, an information display or storage. In another embodiment, the DUPDET 42 receives the duplicate merged data packets from the merger 40 and forwards only one copy of the data packet to the to the endpoint application.

The data packets are communicated to the hospital network 18 via a wireless communication link 46 between the wireless communication interfaces and a wireless access point (WAP) 48. The communication link 46 employs, for example, an IEEE 802.11 protocol including quality of service (QoS) extensions, denoted generically herein as an 802.11-QoS protocol. In some embodiments, the 802.11-QoS protocol conforms with the IEEE 802.11e standard. In some embodiments, the 802.11-QoS protocol conforms with the IEEE 802.11 EDCA standard, where the acronym "EDCA" represents "enhanced distributed channel access." The 802.11-QoS protocol may also employ a subset of the standard IEEE 802.11e protocol (i.e., some features not implemented), or may employ a superset of the standard IEEE 802.11e protocol (additional features added), or may employ a modified protocol based on IEEE 802.11e but with some features added to the standard and some standard features not implemented. It will be appreciated that the communication links 46 are illustrative examples, and that typically the communication system complying with the 802.11-QoS protocol may support several, several dozen, or more such communication links. Similarly, while the single WAP 48 is illustrated, typically the communication system complying with the 802.11-QoS protocol may include one, two, three, four, ten, twenty, or more wireless access points distributed through the hospital or other medical setting to provide desired coverage area for the communication system. In a preferred embodiment, the wireless communication interfaces may communicate with the same WAP 48 or different WAP 48' in a different wireless communication interface through a different wireless protocol.

Figure 2:
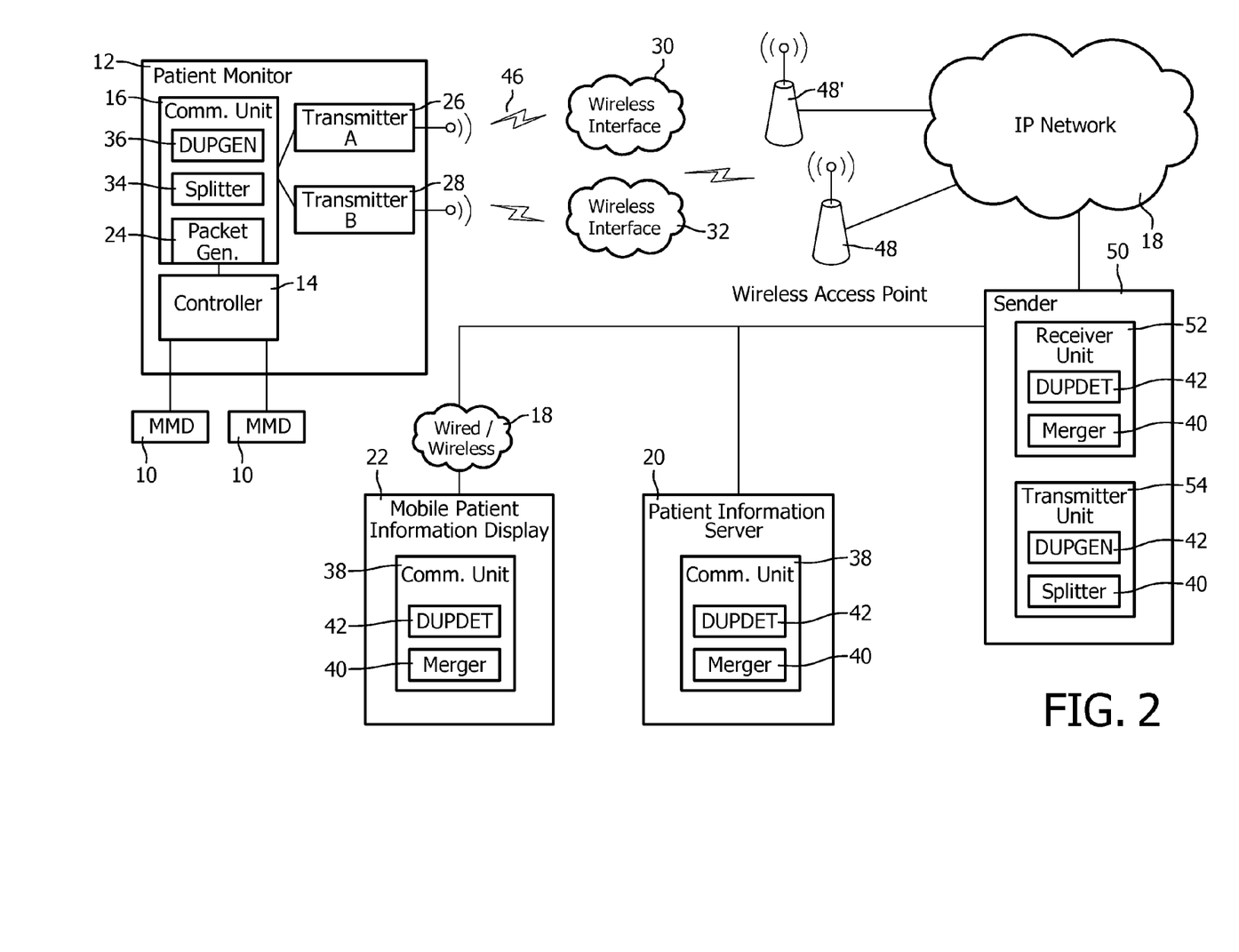

As illustrated in FIG. 2, a sender 50 may also transmit the data packets to the patient information server 20 and the mobile patient information displays 22. During a network handover, the PMD 12 transmits the data packets to the sender 50. The receiving unit 52 of the sender 50 includes a merger 40 and a DUPDET 42. The merger 40 merges together the modified data packets into a single data stream that accurately represents the data packets. The DUPDET 42 receives the duplicate data packets transmitted over the multiple wireless communication interfaces and forwards only one copy of the data packet to the transmitter unit 54. In another embodiment, the DUPDET 42 receives the duplicate merged data packets from the merger 40 and forwards only one copy of the data packet to the transmitter unit 54. The transmitter unit 54 includes a splitter 34 and DUPGEN 36. The DUPGEN 36 creates duplicates of the data packets and transmits the duplicate data packets through the hospital network 18 to the patient information server 20 and the mobile patient information displays 22 on multiple wireless or wired communication interfaces on the mobile patient information display server and patient information server. In one embodiment, the splitter 34 modifies the duplicate data packets created by the DUPGEN 36 with the most appropriate packet size for each communication interface. The communication link between the PMD 12, sender 50, the patient information server 20 and the mobile patient information displays 22 could be made using industry standard protocols such as SIP. In one embodiment, the sender 50 establishes a connection with the PMD 12, the patient information server 20 and the mobile patient information displays 22 using SIP protocols. In another embodiment, the sender 50 establishes a connection with the PMD 12, the patient information server 20 and the mobile patient information displays 22, using H.323 protocol. The connections could be uni-directional (send or receive only) or send and receive. In one embodiment, the sender 50 could transmit the real-time data using RTP (IETF RFC 3550) protocol.

It will be appreciated that each of the PMD 12, the sender 50, the WAP 48, the hospital IP network 18, the patient information server 20 and the mobile patient information display systems 22 described in various embodiments and figures herein include a memory or computer-readable medium (not shown) that stores, and one or more processors (not shown) that execute, computer-executable instructions for performing the various functions, actions, steps, methods, etc., described herein. The memory may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

Figure 3:
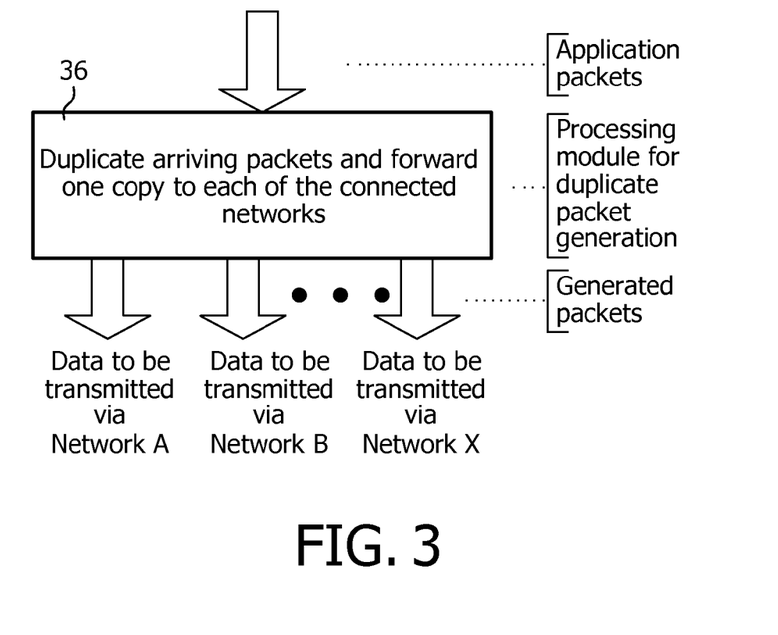
FIG. 3 is a pictorial illustration of the operation of a packet duplicate generator in accordance with the present application.
Figure 4:
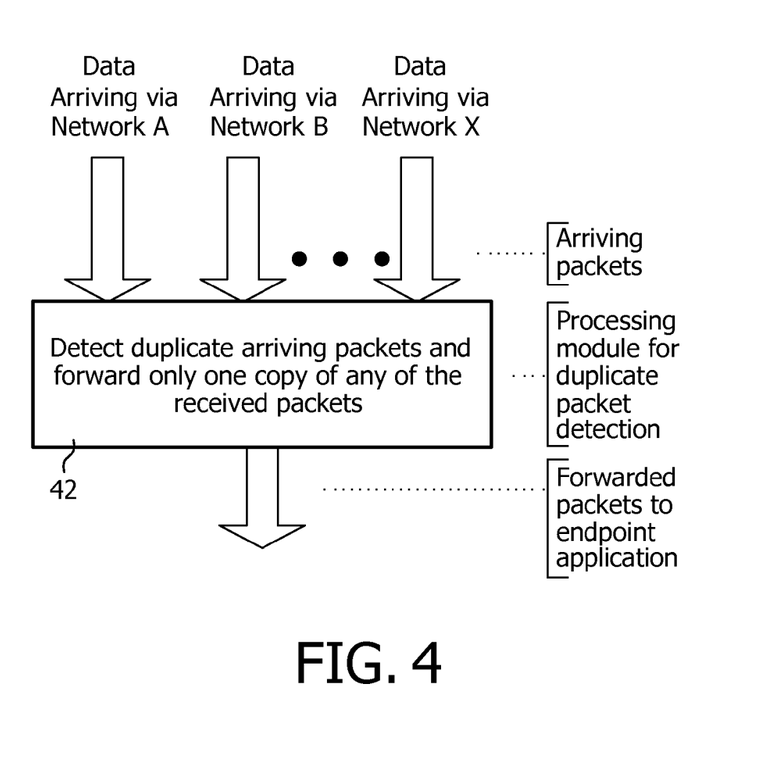
FIG. 4 is a pictorial illustration of the operation of a packet duplicate detector in accordance with the present application.

With reference to FIG. 3, illustrated is a pictorial representation of the DUPGEN 36 operation. Data packets are received at the DUPGEN 36. The DUPGEN 36 duplicates arriving data packets generated by the packet generator 24 and forwards one copy of the duplicated data packets to each of the connect wireless or wired communication interfaces. The duplicated data packets are then transmitted via the various wireless or wired communication interfaces. In another embodiment, the duplicated packets are further modified by the splitter 34 to resize the packets to the most appropriate packet size for each of the various communication interfaces and then transmitted via the various interfaces. With reference to FIG. 4, illustrated is a pictorial representation of the DUPDET 42. Duplicate data packets are received at the DUPDET 42 via the various communication interfaces. The DUPDET 42 detects the arriving duplicate data packets and forwards one copy of any of the received packets to an endpoint application. In another embodiment, the received data packets are received at the merger 40 which merges together the modified data packets into a single data stream that accurately represents the data packets before being received at the DUPDET 42.

Because of the duplication and merger occurs at the application layer, support from the underlying wireless or wired networks to support seamless handovers is not needed. The underlying networks need not be aware of that a particular data stream belongs to a particular device which is transitioning or may transition to another network. The networks would not need to have additional functionality, beyond what is needed to support connections within the same type of network, to support seamless handovers across the networks.

In one embodiment, duplicate data packets of the same size are transmitted through multiple interfaces simultaneously. In another embodiment, networks with higher bandwidths or data rates transmit packets with large number of bytes, but less frequently, to conserve power consumption. This is due to the fact that overhead remains the same for transmitting a small or large packet, therefore, efficiency increases when transmitting larger packets. In contrast, for networks with narrow bandwidth, the maximum packets size is limited by the network protocol, or conversely, large packet size may introduce long delays which might be unacceptable. Therefore, generally, for a given application, there is an optimal packet size and inter packet generation delay for a given network characteristics. In another embodiment, a network which has higher bit error rates transmits smaller packets and less inter-packet arrival rates. Conversely, it is also true that in networks which have low bit error rate, it is more advantageous to transmit bigger packets with large packet inter-arrival rate. This is due to the fact that the larger a packet is the greater the probability of a packet being corrupted. Hence, a smaller packet size is desirable for a network with high probability of bit error rate to reduce probability of un-correctable packet errors.

Figure 5:
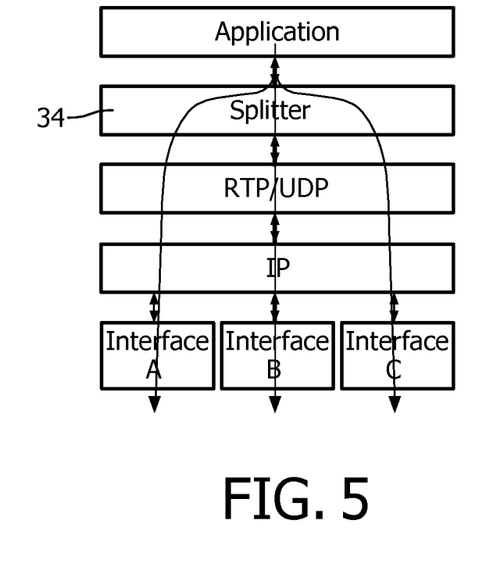
FIGS. 5 and 6 are pictorial illustrations of the operation of a packet splitter in accordance with the present application.
Figure 6:
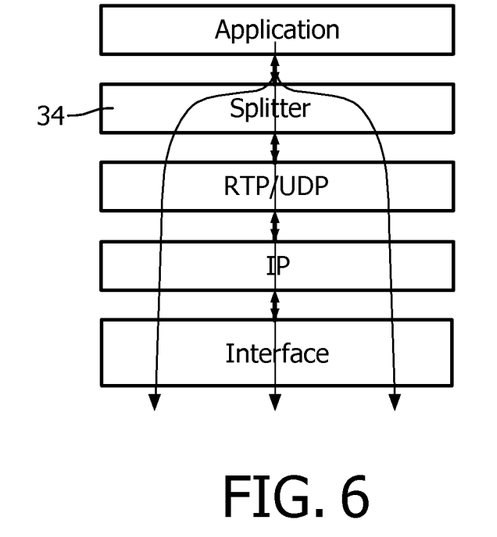

With reference to FIGS. 5 and 6, illustrated is a pictorial representation of the splitter 34. The splitter 34 creates packets with the most appropriate packet size for each communication interface. The determination of the most appropriate packet size, and inter-arrival delay, for each communication interface depends on the each interface's power consumption characteristics, bandwidth and bit error rate, the application delay requirements, and the interface's maximum transmission units (MTU) size among others. The splitter 34 may modify the data packets by grouping them together into larger packet which is then transmitted over the network in a process called aggregation. The splitter 34 may also modify the data packets by fragmenting them into smaller packets in a process called fragmentation. In one embodiment shown in FIG. 5, the splitter 34 has three network interfaces each of which transmits the application flow with the most appropriate network packet size and packet inter arrival time. In one embodiment, the packet size is a fixed integer number of bytes. In another embodiment, the packet size is specified in a range from a minimum to a maximum number of bytes. If the interface-specific packet size or the maximum packet size in the range is larger than the application packet size, then multiple application packets are aggregated into a single packet sent over the network. In another embodiment, the interface-specific splitter aggregates application packets to meet an interface specific, pre-determined packet size range and inter-arrival time range by combining an integer number of application packets. In another embodiment, the splitter 34 aggregates one or more application packets or parts thereof into interface specific packets, i.e. aggregated packets comprise complete packets and fraction of packets. The aggregation process needs to ensure that the maximum allowed application transmission delay is not violated.

To be able to merge the different data flows with the merger 40, an application header is added to the application payload. The header may include a timestamp, which specifies the time covered by the payload, e.g. in an RTP the timestamp reflects the sampling instant of the first byte of the payload. In one embodiment, the timestamp in the first aggregated packet transmitted over an interface is the time when the application packet arrived. In the case where packets are fragmented the timestamp in subsequent packets is calculated as follows:

$$T_s(n) = T_s(n-1) + \frac{P(n-1)}{S*R}$$

where:
$T_s(n)$: Timestamp in nth fragment
$P(n)$: Size of nth fragment in bytes
S: Sample size in bytes
R: Sampling rate in Hz
For aggregated packets, the timestamp is the timestamp of the first application packet in the tx-buffer. In case the aggregated packet is transmitted because the tx-buffer is full, the timestamp of the next aggregated packet is calculated as follows:

$$T_s(n) = T_s(l) + \frac{P_{frag}(l)}{S*R}$$

where:
$T_s(S)$: Timestamp next aggregated packet
$T_s(l)$: Timestamp last application packet fragment in tx-buffer
$P_{frag}(l)$: Size of last application fragment in tx-buffer
S: Sample size in bytes
R: Sampling rage in Hz
In another embodiment shown in FIG. 6, packets arriving from the local application are split into three flows and transmitted over the same communication interface. If the desired interface-specific packet size or the maximum of the packet size range is smaller than the application packet size, the application packet is fragmented in two or more packets sent over the network. A header with a timestamp and the packet size is added in the beginning of each application layer fragment.

Figure 7:
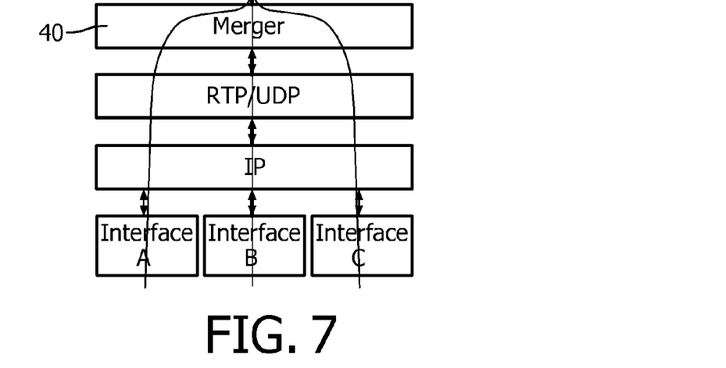
FIG. 7-9 are pictorial illustrations of the operation of a packet merger.
Figure 8:
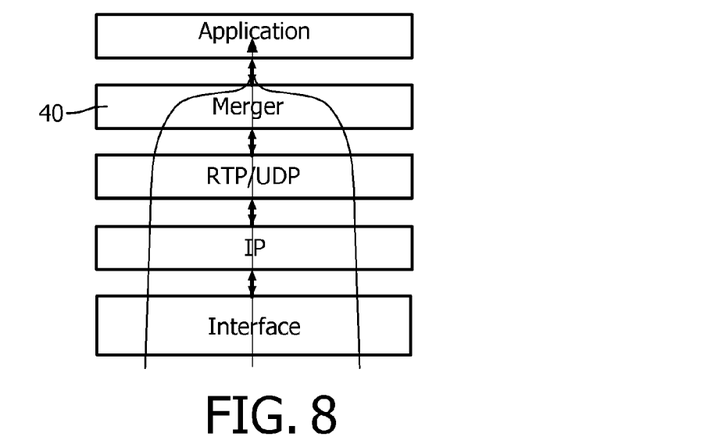
Figure 9:
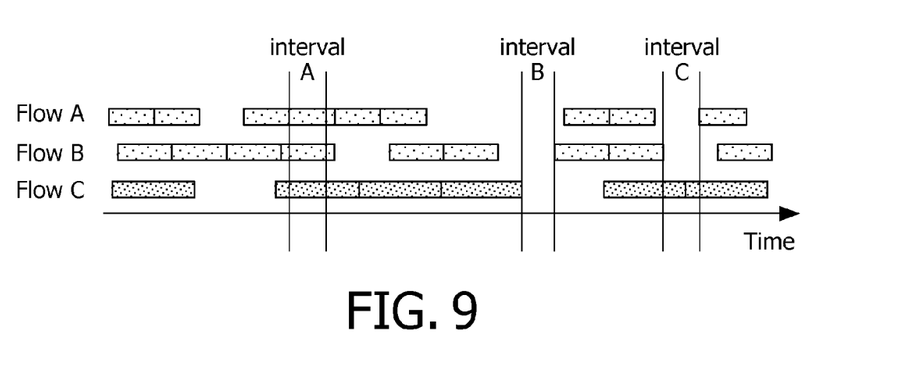

With reference to FIGS. 7-9, illustrated is a pictorial representation of the merger 40. In one embodiment shown in FIG. 7, the merger 40 has three communication interfaces each of which receives one data flow. In one embodiment shown in FIG. 8, the merger 40 receives three data flows which are then merged and sent to the endpoint application. As shown in FIG. 9, the merging process strives to combine the data received through different packet flows, each of which may use different packet sizes, into the most complete representation possible of the original data flow generated by the transmitter side. For illustration purposes, consider the application data received via three flows over some time as shown in FIG. 9. Three flows are shown in the figure: 1) Flow A; 2) Flow B; and, 3) Flow C. Each of the flow has a different packet size, represented in the figure by different block lengths, and different packet error rate, represented in the figure by different gap sizes in between the blocks. Note, that each flow, because it traverses over a different wireless link technology, also has a different transmission delay and jitter, which is not depicted in the figure. FIG. 9 also shows three exemplary time intervals A, B and C. During time interval A, data is received from all the three flows; during time interval B, no data is received, and, during time interval C, data is received only from Flow C. The header of the received packets may include a timestamp, and combined with the packet size information and sampling rate information, together could to determine the sampling time interval covered by a received packet. In one embodiment, the sampling rate information is exchanged during session setup protocol. In another embodiment, the sampling rate information is contained within each packet. Duplicate packets from multiple received packets are identified and only one copy of the duplicate packets is retained. The packets are ordered in the order of sampling time. The process continues until it is time to forward the reconstructed data to the application. In one embodiment, in the case of data missing for some portion of the time, the data could be marked as NULL (not received), or it could be interpolated between adjacent sets of data or it could be filled by repetition of the adjacent data. In another embodiment, if a packet is received, which is outside the range of the time covered by the receive buffer then it could be discarded. The range of the time covered by the received buffer could be updated dynamically in relation to current time or the range of the time covered by the received buffer could be updated at regular intervals of time.

Figure 10:
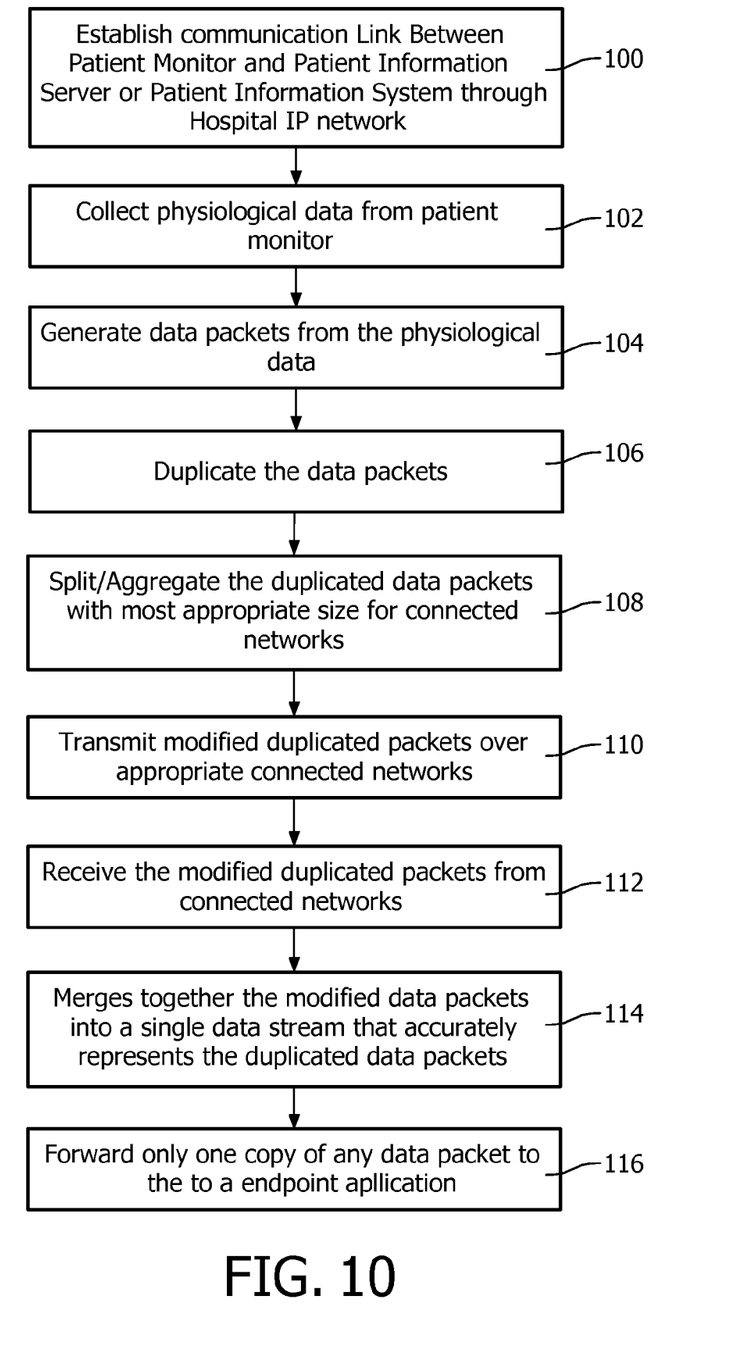
FIG. 10 is a flowchart diagram of the operation of a patient monitoring system in accordance with the present application.

With reference to FIG. 10, illustrated is a flowchart diagram of the operation the patient monitoring system. In a step 100, a communication link is established between patient monitor and patient information server or patient information system through hospital IP network. Physiological data is collected by the patient monitor in a step 102. In a step 104, data packets are generated from the physiological data. In a step 106, the data packets are duplicated. In a step 108, the duplicate data packets are split or aggregated with the most appropriate size for the connected networks. The modified duplicated data packets are then transmitted over the appropriate connected networks in a step 110. In a step 112, the modified duplicated packets are received. The modified duplicated data packets are merged into a single data stream that accurately represents the duplicate data packets in a step 114. In a step 116, one copy of any data packet is forwarded to the to an endpoint application.

Figure 11:
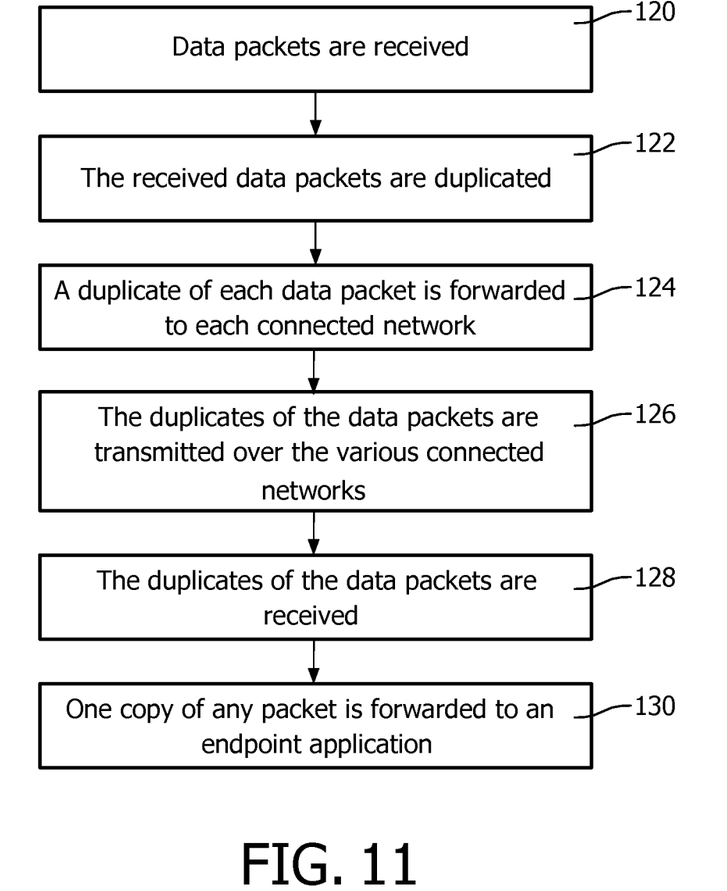
FIG. 11 is a flowchart diagram of the operation of a packet duplicate generator and detector in accordance with the present application.

With reference to FIG. 11, illustrated is a flowchart diagram of the operation of the DUPGEN and DUPDET. In a step 120, data packets are received. The received data packets are duplicated in a step 122. In a step 124, a duplicate of each data packet is forwarded to each connected network. The duplicates of the data packets are transmitted over the various connected networks in a step 126. In a step 128, the duplicates of the data packets are received. In a step 130, one copy of any packet is forwarded to an endpoint application.

Figure 12:
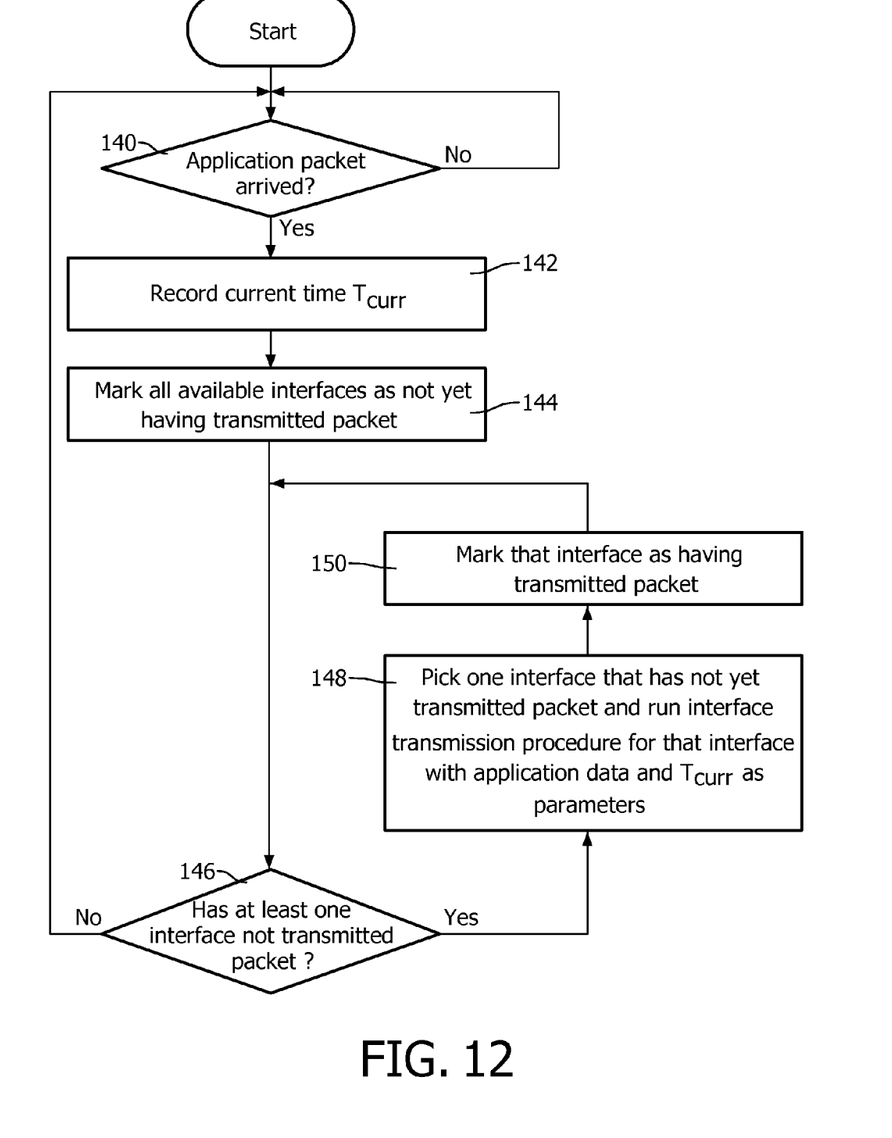
FIG. 12-14 are flowchart diagrams of the operation of a packet splitter in accordance with the present application.

With reference to FIG. 12, illustrated is a flowchart diagram of the operation the splitter unit. In a step 140, it is determined whether a data packet has arrived. In a step 142, the current time $T_{current}$ is recorded. All available interfaces as not yet having transmitted a packet are marked in a step 144. In a step 146, it is determined whether at least one interface has not transmitted a packet. If at least one interface has transmitted a packet then it is determined whether a packet has arrived in a step 140. If at least one interface has not transmitted a packet then an interface that has not yet transmitted a packet is picked and the interface transmission procedure for that interface with application data and $T_{current}$ as a parameter is run in a step 148. In a step 150, that interface is marked as having transmitted a packet.

Figure 13:
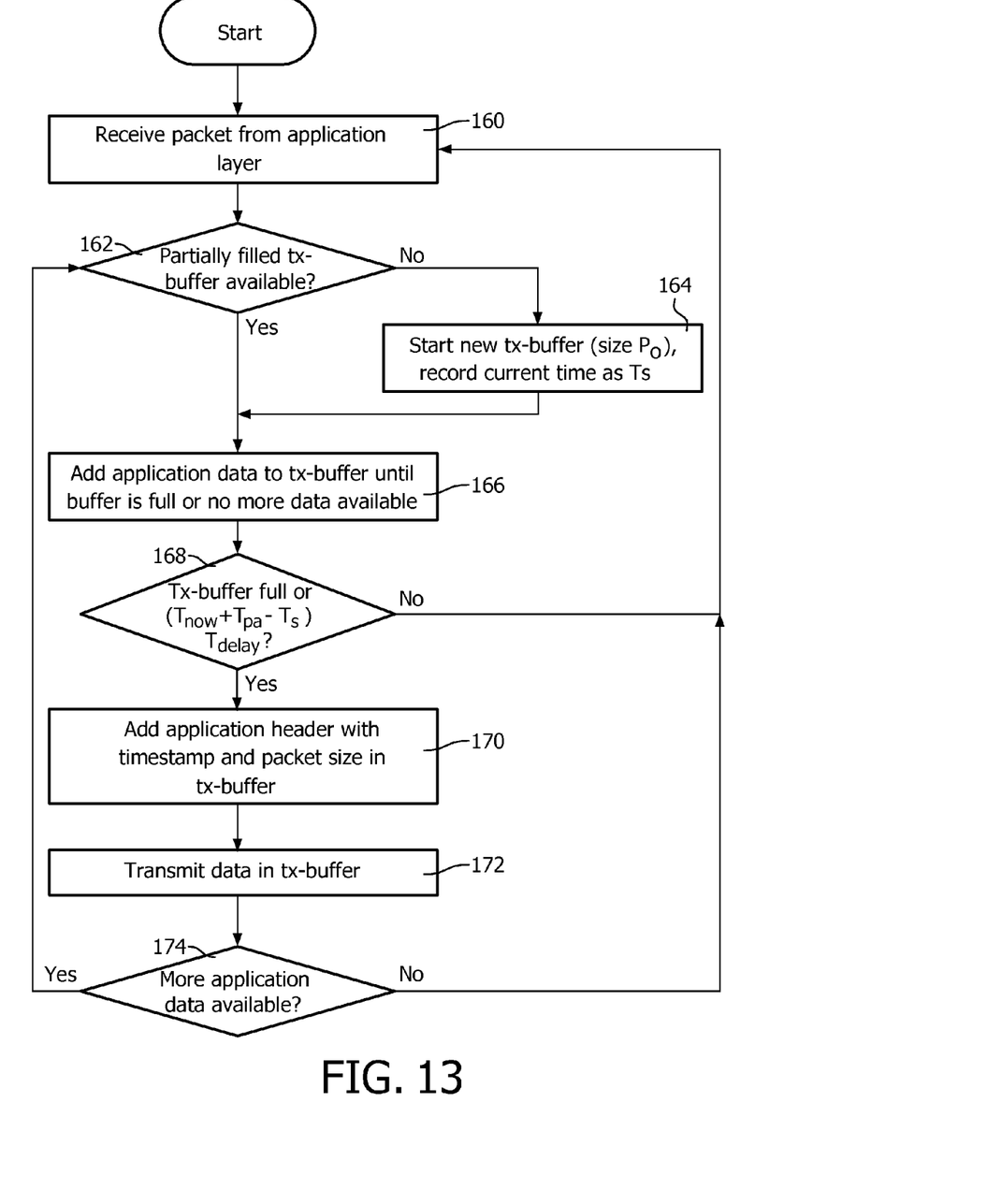

With reference to FIG. 13, illustrated is a flowchart diagram of the aggregation process. In a step 160, a packet is received from the application layer. In a step 162, it is determined if the partially filled buffer is available. If the buffer is not available then a new buffer (size of Po) is starting and the current time is recorded as Ts in a step 164. If the partially filled buffer is available then data is added to the buffer until the buffer is full or not more data is available in a step 166. In a step 168, it is determined whether the buffer is full. If the buffer is not full then packets are received from the application layer in step 160. If the buffer is full then an application header is added with a timestamp and packet size in the buffer in a step 170. In a step 172, the data in the buffer is transmitted. In a step 174, it is determined whether more application data is available. If not more data is available, then packets are received from the application layer in step 160. If more data is available, then it is determined whether the partially filled buffer is available in step 162.

Figure 14:
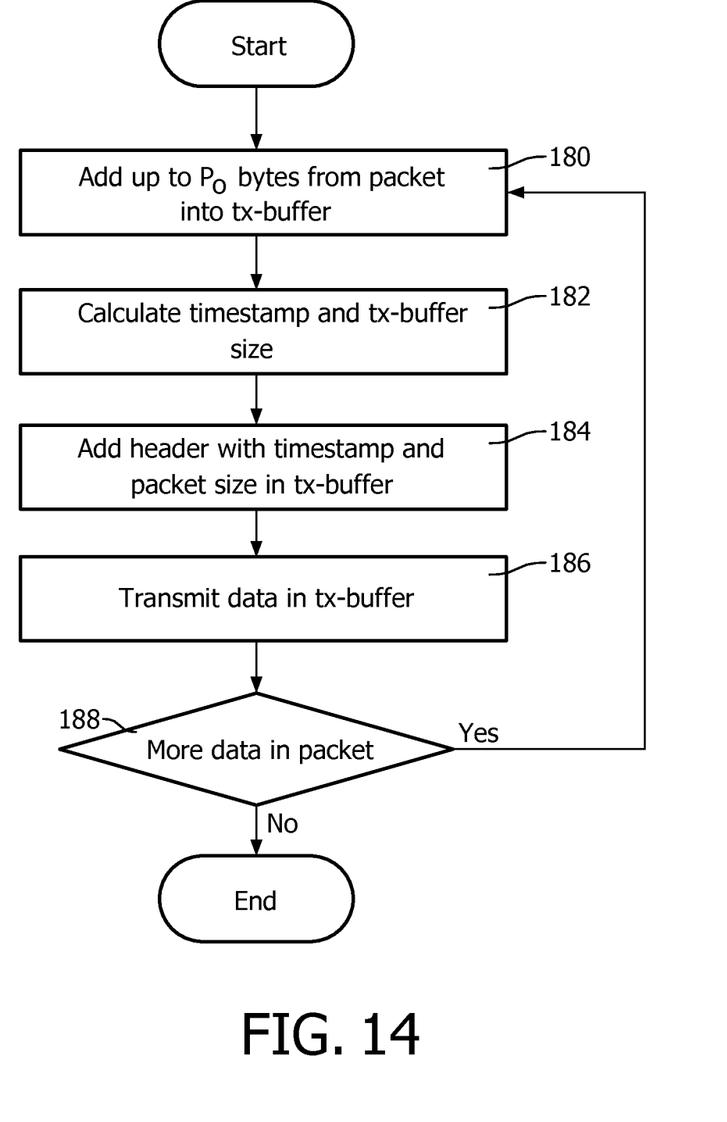

With reference to FIG. 14, illustrated is a flowchart diagram of the fragmentation process. In a step 180, up to $P_0$ bytes are added from the packet into the buffer. In a step 182, a timestamp and buffer size is calculated. A header is added with the timestamp and packet size in the buffer in a step 184. In a step 186, the data in the buffer is transmitted. In a step 188, it is determined whether more data is in the packet. If more data is in the packet, then up to $P_0$ bytes are added from the packet into the buffer in step 180.

Figure 15:
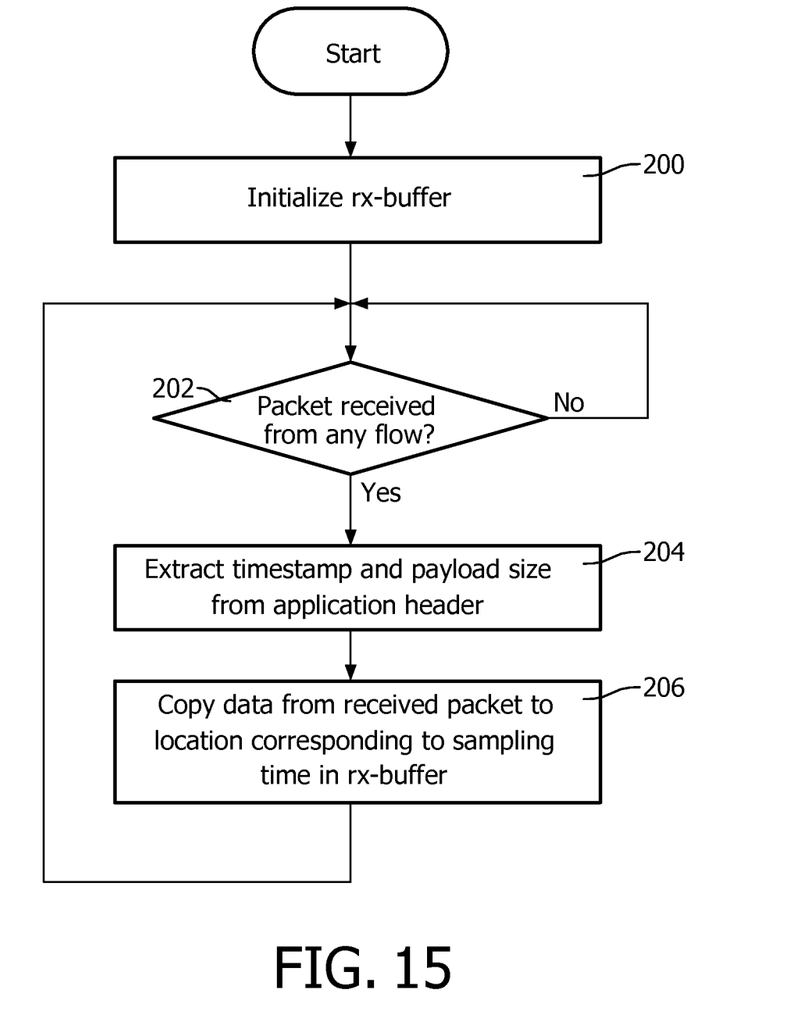
FIG. 15 is a flowchart diagram of the operation of a packet merger in accordance with the present application.

With reference to FIG. 15, illustrated is a flowchart diagram of the process for filling the receive buffer. In a step 200, a buffer is initialized. In a step 202, it is determined whether the packet received any flow. If the packet did receive flow, then a timestamp and payload size is extracted from the application header in a step 204. Data from the received packet is copied to a location corresponding to the sampling time in the buffer in a step 206.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A method for transmitting physiological data, comprising:
    establishing a communication link between a multi-mode patient monitoring device and a plurality of Internet protocol (IP) networks;
    collecting physiological data collected by the patient monitoring device at a sampling rate;
    generating data packets including the collected physiological data as data payloads:
    duplicating the generated data packets;
    transmitting the duplicated data packets over the plurality of networks;
    receiving the transmitted duplicated data packets;
    after the receiving step, determining a sampling time interval of the collected physiological data payload of each received duplicate data packet from a timestamp of the packet, packet size information, and the physiological data acquisition sampling rate of the collected physiological data payload of each received duplicate data packet;
    generating a single set of data from the collected physiological data payloads of the duplicated data packets by merging the data payloads of the received duplicate data packets using the sampling time intervals of the collected physiological data payloads determined for the received duplicate data packets; and
    forwarding the single set of data to an end application.

2. The method according to claim 1, further including:
    before the transmitting step, resizing the duplicated data packets to the most appropriate size for transmitting on each of the plurality of networks; and
    after the receiving step, merging together the resized data packets into a data stream that accurately represents the duplicated data packet.

3. The method according to claim 1, wherein the plurality of networks include at least one of a IP Multimedia Subsystem (IMS) GPRS, UMTS, CDMA2000, IS-95, GSM, CDMA, CDMA 1x, CDMA 1xEV-DO, WiMAX, IEEE 802.11, IEEE 805.15, IEEE 802.16, IEEE 802.21 Wi-Fi, UMTS over W-CDMA, UMTS over TDD, CDMA 3xEV-DO, HSPA D, HSPA U, EDGE, Bluetooth, Zigbee, UWB, LTE and Wi-Bree network.

4. A computer-readable medium carrying software for controlling one or more processors to configure and perform the method according to claim 1.

5. The method according to claim 1, wherein the sampling time interval has duration $$\frac{P}{S*R},$$

wherein:
P is the packet size;
S is a sample size; and
R is the physiological data acquisition sampling rate.

6. The method according to claim 2, wherein the resizing is at least one of an aggregation and fragmentation process.

7. The method according to claim 2, wherein the most appropriate packet size depends on at least one of each network's power consumption characteristics, bandwidth and bit error rate, the application delay requirements, and the interface's maximum transmission units (MTU) size.

8. The method according to claim 2, wherein the most appropriate packet size depends on each network's power consumption characteristics.

9. A patient monitor comprising:
at least one monitoring device which collects patient data about a patient;
a packet generator which generates data packets from the patient data collected from the patient;
a packet duplicator which generates duplicates of the data packets; and
a communication unit which transmits the data packets over a hospital Internet protocol (IP) network,
wherein the communication unit includes a first transmitter for transmitting the data packets using a first wireless network and a second transmitter for transmitting the data packets using a second wireless network; and
the first and second transmitters are configured to transmit duplicate data packets simultaneously;
wherein the packet splitter is configured to resize the data packets to a packet size in accordance with each network's power consumption characteristics.

10. The patient monitor according to claim 9, wherein the communication unit further includes:
a packet splitter which resizes the duplicated data packets to the most appropriate size for each of the first and second wireless networks.

11. The patient monitor according to claim 9, wherein the first and second networks include at least one of a IP Multimedia Subsystem (IMS) GPRS, UMTS, CDMA2000, IS-95, GSM, CDMA, CDMA 1x, CDMA 1xEV-DO, WiMAX, IEEE 802.11, IEEE 802.15, IEEE 802.16, IEE 802.21, Wi-Fi, UMTS over W-CDMA, UMTS over TDD, CDMA 3xEV-DO, HSPA D, HSPA U, EDGE, Bluetooth, Zigbee, UFB, LTE and Wi-Bree network.

12. The patient monitor according to claim 9, wherein the patient monitor is a battery powered ambulatory patient worn monitor.

13. The patient monitor according to claim 9, wherein the packet splitter is configured to resize the data packets using at least one of an aggregation process and a fragmentation process.

14. A patient monitoring system, comprising:
a plurality of the patient monitors according to claim 9; and a patient information server in communication with the hospital IP network to receive the data packets that were transmitted via the first and second networks and at least one of: (i) generate a display based on the data packets received and (ii) store the patient data about the patient.

15. The patient monitoring system according to claim 14, wherein the patient information server includes:
a packet merger which merges the resized data packets into a data stream that accurately represents the duplicated data packet; and
a duplicate packet detector for forwarding one of the duplicated data packets to the patient information server application.

16. The patient monitoring system according to claim 14, further including:
a sender which receives data packets from the plurality of patient monitors and transmits the data packets to a mobile information display.

17. The patient monitoring system according to claim 16, wherein the sender includes:
a receiving unit including:
a packet merger which merges the resized data packets into a data stream that accurately represents the duplicated data packet; and
a duplicate packet detector for forwarding one of the duplicated data packets to the mobile information display; and
a transmitting unit including:
a packet duplicator which generates duplicates of the data packets; and
optionally, a packet splitter which resizes the duplicated data packets to the most appropriate size for each of the first and second wireless networks.

18. An apparatus comprising:
a monitoring device configured to collect physiological data at a sampling rate; and
a data recipient device configured to connect with the monitoring device via a plurality of Internet protocol (IP) network connections;
wherein the monitoring device includes a monitoring device processor programmed to:
generate an original data packet stream of data packets from the collected physiological data wherein each data packet has a packet size and includes a data payload of physiological data and a time stamp that together with the packet size and the sampling rate specifies a time interval covered by the data payload,
duplicate the data packets to generate duplicate data packet streams, and
transmit each duplicate data packet stream via a different IP network connection of the plurality of IP network connections; and
wherein the data recipient device including a recipient device processor programmed to:
receive the duplicate data packet streams from the monitoring device via the plurality IP network connections;
merge the received duplicate data packet streams into a single data stream representing the original data packet stream by determining the time intervals covered by the data payloads of the duplicate data packets using the physiological data acquisition sampling rate and packet timestamps and packet sizes of the duplicate data packets; and
forward the single data stream to an end application.

19. The apparatus of claim 18 wherein:
the monitoring device processor is further programmed to aggregate or fragment duplicate data packets of at least one duplicate data packet stream prior to transmission based on characteristics of the IP network connection via which the duplicate data packet stream is transmitted.

20. The apparatus of claim 18, wherein the sampling time interval has duration $$\frac{P}{S*R},$$

wherein:
P is the packet size;
S is a sample size; and
R is the physiological data acquisition sampling rate.

* * * * *